United States Patent
Arai et al.

(10) Patent No.: US 10,981,853 B2
(45) Date of Patent: Apr. 20, 2021

(54) METHOD FOR PREPARING α,β-UNSATURATED ALDEHYDE

(71) Applicant: Kao Corporation, Tokyo (JP)

(72) Inventors: Tsubasa Arai, Wakayama (JP); Kensuke Masumura, Wakayama (JP); Kensuke Karasu, Wakayama (JP); Yuki Nakagawa, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/771,409

(22) PCT Filed: Jun. 12, 2018

(86) PCT No.: PCT/JP2018/022404
§ 371 (c)(1),
(2) Date: Jun. 10, 2020

(87) PCT Pub. No.: WO2019/116608
PCT Pub. Date: Jun. 20, 2019

(65) Prior Publication Data
US 2020/0347003 A1    Nov. 5, 2020

(30) Foreign Application Priority Data

Dec. 12, 2017  (JP) .............................. JP2017-237934
May 31, 2018  (JP) .............................. JP2018-104435

(51) Int. Cl.
    *C07C 45/72*    (2006.01)
    *C07C 45/74*    (2006.01)

(52) U.S. Cl.
    CPC ..................................... *C07C 45/74* (2013.01)

(58) Field of Classification Search
    CPC ................................ C07C 45/72; C07C 45/74
    See application file for complete search history.

(56) References Cited

U.S. PATENT DOCUMENTS

| | | | |
|---|---|---|---|
| 5,055,621 A | 10/1991 | Payne | |
| 6,723,883 B1 | 4/2004 | Therre et al. | |
| 2005/0272958 A1 | 12/2005 | Hasegawa et al. | |
| 2007/0093681 A1 | 4/2007 | Noack et al. | |
| 2008/0292879 A1 | 11/2008 | Kumamoto et al. | |
| 2009/0171124 A1 | 7/2009 | Ishida et al. | |
| 2010/0010268 A1 | 1/2010 | Shirasawa et al. | |
| 2015/0284310 A1 | 10/2015 | Arai et al. | |
| 2015/0344391 A1 | 12/2015 | Nishimura et al. | |
| 2016/0289151 A1 | 10/2016 | Arai et al. | |

FOREIGN PATENT DOCUMENTS

| | | |
|---|---|---|
| CN | 101265167 A | 9/2008 |
| CN | 102719638 A | 10/2012 |
| CN | 103539647 A | 1/2014 |
| JP | 3-14535 A | 1/1991 |
| JP | 4-112846 A | 4/1992 |
| JP | 5-168928 A | 7/1993 |
| JP | 2003-511431 A | 3/2003 |
| JP | 2005-342675 A | 12/2005 |
| JP | 2007-513919 A | 5/2007 |

(Continued)

OTHER PUBLICATIONS

International Search Report dated Aug. 21, 2018 in PCT/JP2018/022404 filed on Jun. 12, 2018, 2 pages.
Vashishtha, M. et al., "A novel approach for selective cross aldol condensation using reusable NaOH-cationic micellar systems," Applied Catalysis A: General, vol. 466, 2013, pp. 38-44.

(Continued)

*Primary Examiner* — Sikarl A Witherspoon
(74) *Attorney, Agent, or Firm* — Oblon, McClelland, Maier & Neustadt, L.L.P.

(57) ABSTRACT

The present invention aims to provide a method for preparing an aldehyde, which can prepare a target aldehyde with high selectivity and can also suppress the production of by-products. The present invention relates to a method for preparing an α,β-unsaturated aldehyde. The method includes a step of reacting a compound of formula (I) with a compound of formula (II) to provide an α,β-unsaturated aldehyde of formula (III). An alkali metal hydroxide and an alkanol having 1 to 4 carbon atoms are used in the step. The amount of the alkali metal hydroxide is 8 mol % or more and 12 mol % or less with respect to the compound of formula (I). The total amount of water contained in materials that are used in the reaction is 10 mol % or more and 50 mol % or less with respect to the compound of formula (I).

[Chemical Formula 1]

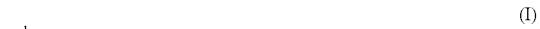

(I)

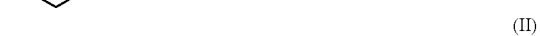

(II)

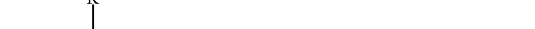

(III)

13 Claims, No Drawings

(56) References Cited

FOREIGN PATENT DOCUMENTS

| JP | 2007-153818 A | 6/2007 |
|----|---------------|--------|
| JP | 4806354 B2 | 11/2011 |
| JP | 4886283 B2 | 2/2012 |
| JP | 2012-126676 A | 7/2012 |
| JP | 5001549 B2 | 8/2012 |
| JP | 5143438 B2 | 2/2013 |
| JP | 2014-9167 A | 1/2014 |
| JP | 2014-118394 A | 6/2014 |
| JP | 2014-139158 A | 7/2014 |
| JP | 2015-143220 A | 8/2015 |

OTHER PUBLICATIONS

Office Action in corresponding Indian Patent Application No. 202017027768 dated Nov. 13, 2020.
N. Sudheesh, et al., "Chitosan as an eco-friendly solid base catalyst for the solvent-free synthesis of jasminaldehyde", Journal of Molecular Catalysis A: Chemical, vol. 321, 2010, pp. 77-82.

METHOD FOR PREPARING α,β-UNSATURATED ALDEHYDE

TECHNICAL FIELD

The present invention relates to a method for preparing an α,β-unsaturated aldehyde.

BACKGROUND ART

An aldehyde is a useful compound as, e.g., a material for a chemical reaction, or an intermediate for perfume, medicine, or agricultural chemicals. In particular, an α,β-unsaturated aldehyde having a specific molecular weight is useful in itself as a fragrance material, and further is also used as a raw material for derivatives with different fragrance notes.

As a method for preparing an aldehyde, e.g., dehydrogenation or oxidation using alcohol as a raw material has conventionally been known. In particular, a cross-aldol condensation reaction between two types of aldehydes is frequently used as a method for preparing an α,β-unsaturated aldehyde. Moreover, various studies have been made on the reaction conditions of the cross-aldol condensation reaction.

For example, Patent Document 1 discloses the continuous production of cinnamaldehyde and dihydrocinnamaldehyde. In this method, benzaldehyde derivatives are continuously reacted with alkanals in a plant that includes a plurality of reactors in a cascade system.

Patent Document 2 discloses a method for preparing an α-substituted cinnamaldehyde. This method is performed in a solvent containing glycol.

On the other hand, Patent Document 3 discloses a method for preparing 2,3-cis-substituted 2-arylpropenals by condensing a 2-arylacetaldehyde with a nonenolizable aldehyde. In this method, a solvent contains a specific amount of moisture.

PRIOR ART DOCUMENTS

Patent Documents

Patent Document 1: JP 2003-511431 A
Patent Document 2: JP H3(1991)-14535 A
Patent Document 3: JP 2007-513919 A

DISCLOSURE OF INVENTION

Problem to be Solved by the Invention

The cross-aldol condensation reaction is known to cause side reactions such as dimerization (self-aldol condensation reaction) and disproportionation (Cannizzaro reaction) between the same type of aldehydes. If the side reactions proceed, it is difficult to isolate the target aldehyde, and the yield is reduced.

With the foregoing in mind, the present invention provides a method for preparing an α,β-unsaturated aldehyde, which can prepare a target aldehyde with high selectivity and can also suppress the production of by-products.

Means for Solving Problem

The present inventors found that it was possible to obtain the target aldehyde with high selectivity and to suppress the production of by-products in the cross-aldol condensation reaction by adjusting the total amount of water contained in the materials that were used in the reaction to a specific amount.

The present invention provides a method for preparing an α,β-unsaturated aldehyde, including a step of reacting a compound of formula (I) with a compound of formula (II) to provide an α,β-unsaturated aldehyde of formula (III), wherein an alkali metal hydroxide and an alkanol having 1 to 4 carbon atoms are used in the step,
an amount of the alkali metal hydroxide is 8 mol % or more and 12 mol % or less with respect to the compound of formula (I), and a total amount of water contained in materials that are used in the reaction is 10 mol % or more and 50 mil % or less with respect to the compound of formula (I),
[Chemical Formula 1]

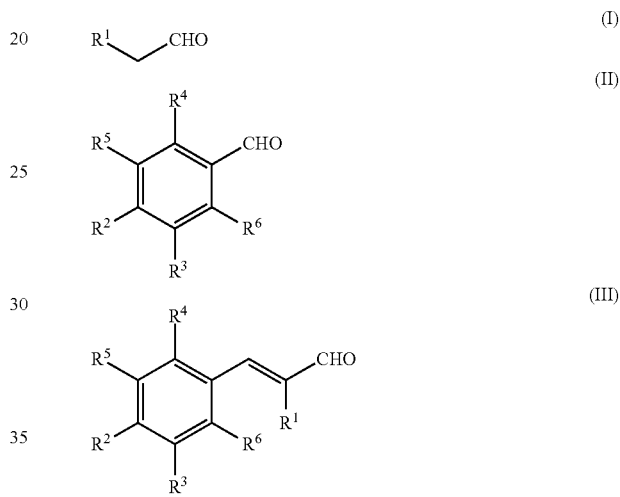

In the above formula, $R^1$ represents a hydrogen atom or an alkyl group having 1 to 10 carbon atoms,
$R^2$ represents a hydrogen atom, an alkyl group having 1 to 6 carbon atoms, or an alkoxy group having 1 to 6 carbon atoms,
$R^3$ represents a hydrogen atom, or
$R^2$ and $R^3$ form 1,3-dioxolane together with carbon atoms to which $R^2$ and $R^3$ are bound, and
$R^4$, $R^5$, and $R^6$ each independently represent a hydrogen atom or an alkyl group having 1 to 3 carbon atoms.

Effects of the Invention

The present invention can provide a method for preparing an α,β-unsaturated aldehyde, which can prepare a target aldehyde with high selectivity and can also suppress the production of by-products.

DESCRIPTION OF THE INVENTION

In the method for preparing an α,β-unsaturated aldehyde of the present invention, the cross-aldol condensation reaction between the compound of formula (I) and the compound of formula (II) involves the use of a specific amount of water in addition to the alkali metal hydroxide and the alkanol that serve as catalysts.
[Compound of Formula (I)]
In the compound of formula (I), $R^1$ represents a hydrogen atom or an alkyl group having 1 to 10 carbon atoms. $R^1$ is preferably an alkyl group having 1 to 10 carbon atoms. From the viewpoint of the reactivity of the cross-aldol condensation reaction and the usefulness of the aldehyde to be prepared as a fragrance material, the alkyl group having 1 to 10 carbon atoms is preferably an alkyl group having 2 or more carbon atoms, and more preferably an alkyl group having 3 or more carbon atoms. Furthermore, the alkyl group having 1 to 10 carbon atoms is preferably an alkyl group having 8 or less carbon atoms, and more preferably an alkyl group having 7 or less carbon atoms. The alkyl group having 1 to 10 carbon atoms may be either a straight-chain alkyl group or a branched-chain alkyl group, and is preferably a straight-chain alkyl group. Examples of the alkyl group having 1 to 10 carbon atoms include methyl, ethyl, n-propyl, isopropyl, 2-methylpropyl, n-butyl, t-butyl, pentyl, hexyl, heptyl, octyl, nonyl, and decyl. Examples of the compound of formula (I) include acetaldehyde, propionaldehyde, butanal, pentanal, hexanal, octanal, nonanal, decanal, and dodecanal. From the viewpoint of the reactivity of the cross-aldol condensation reaction, the compound of formula (I) is preferably propionaldehyde, butanal, pentanal, hexanal, octanal, nonanal, or decanal, more preferably pentanal, hexanal, octanal, nonanal, or decanal, and even more preferably pentanal, hexanal, octanal, or nonanal.

[Compound of Formula (II)]

In the compound of formula (II), $R^2$ represents a hydrogen atom, an alkyl group having 1 to 6 carbon atoms, or an alkoxy group having 1 to 6 carbon atoms. $R^2$ is preferably a hydrogen atom or an alkyl group having 1 to 6 carbon atoms, and more preferably a hydrogen atom-group. From the viewpoint of the reactivity of the cross-aldol condensation reaction and the usefulness of the aldehyde to be prepared as a fragrance material, the alkyl group having 1 to 6 carbon atoms is preferably an alkyl group having 1 or more carbon atoms. Furthermore, the alkyl group having 1 to 6 carbon atoms is preferably an alkyl group having 5 or less carbon atoms, and more preferably an alkyl group having 4 or less carbon atoms. Examples of the alkyl group having 1 to 6 carbon atoms include methyl, ethyl, n-propyl, isopropyl, 2-methylpropyl, n-butyl, t-butyl, pentyl, and hexyl. The alkoxy group having 1 to 6 carbon atoms is an alkyloxy group having 1 to 6 carbon atoms. Examples of the alkoxy group having 1 to 6 carbon atoms include methoxy, ethoxy, n-propyloxy, isopropyloxy, 2-methylpropyloxy, n-butyloxy, t-butyloxy, pentyloxy, and hexyloxy. From the viewpoint of the reactivity of the cross-aldol condensation reaction and the usefulness of the aldehyde to be prepared as a fragrance material, the alkoxy group having 1 to 6 carbon atoms is preferably an alkoxy group having 1 to 5 carbon atoms, and more preferably an alkoxy group having 1 to 4 carbon atoms.

In the composition of formula (II), when $R^2$ and $R^3$ form 1,3-dioxolane together with carbon atoms to which $R^2$ and $R^3$ are bound, the compound of formula (II) is represented by the following formula,

[Chemical Formula 2]

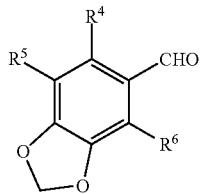

In the above formula, $R^4$, $R^5$, and $R^6$ are as defined in the formula (II).

In the compound of formula (II), $R^4$, $R^5$, and $R^6$ each independently represent a hydrogen atom or an alkyl group having 1 to 3 carbon atoms. $R^4$, $R^5$, and $R^6$ are preferably hydrogen atoms. From the viewpoint of the usefulness of the aldehyde to be prepared as a fragrance material, the alkyl group having 1 to 3 carbon atoms is preferably an alkyl group having 1 to 2 carbon atoms, and more preferably an alkyl group having 1 carbon atom. Examples of the alkyl group having 1 to 3 carbon atoms include methyl, ethyl, n-propyl, and isopropyl.

The compound of formula (II) is preferably, e.g., any of the following compounds.

[Chemical Formula 3]

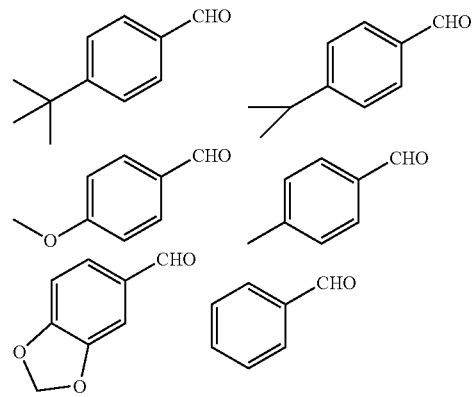

In the present invention, the amount of the compound of formula (II) used is preferably 1 equivalent or more, and more preferably 1.5 equivalents or more with respect to the compound of formula (I). Furthermore, the amount of the compound of formula (II) used is preferably 5 equivalents or less, and more preferably 3 equivalents or less with respect to the compound of formula (I)

[Alkali Metal Hydroxide]

In the present invention, the alkali metal hydroxide may be, e.g., lithium hydroxide, sodium hydroxide, or potassium hydroxide. From the viewpoint of reaction efficiency, the alkali metal hydroxide is preferably sodium hydroxide or potassium hydroxide, and more preferably potassium hydroxide.

In the present invention, the amount of the alkali metal hydroxide is 8 mol % or more and 12 mol % or less with respect to the compound of formula (I). From the viewpoint of reaction efficiency, the amount of the alkali metal hydroxide is preferably 9 mol % or more and preferably 11 mol % or less with respect to the compound of formula (I). This is because the disproportionation of the compound of formula (II) can be suppressed by reducing the amount of the alkali metal hydroxide, and thus the production of by-products can be suppressed.

[Alkanol Having 1 to 4 Carbon Atoms]

In the present invention, the alkanol having 1 to 4 carbon atoms is an alkyl alcohol having 1 to 4 carbon atoms. Examples of the alkanol having 1 to 4 carbon atoms include methanol, ethanol, n-propanol, isopropanol, n-butanol, t-butanol, ethylene glycol, propylene glycol, and diethylene glycol. From the viewpoint of reaction efficiency, the alkanol having 1 to 4 carbon atoms is preferably an alkanol having 1 to 3 carbon atoms, and more preferably an alkanol having 1 to 2 carbon atoms. Furthermore, from the viewpoint of reaction efficiency, the alkanol having 1 to 4 carbon atoms is preferably ethanol or methanol, and more preferably methanol.

In the present invention, from the viewpoint of achieving high reaction efficiency while suppressing a side reaction, the amount of the alkanol having 1 to 4 carbon atoms is preferably 300 mol % or more, and more preferably 350 mol % or more with respect to the compound of formula (I). Furthermore, the amount of the alkanol having 1 to 4 carbon atoms is preferably 500 mol % or less, and more preferably 450 mol % or less with respect to the compound of formula (I). The amount of the alkanol having 1 to 4 carbon atoms is preferably 300 mol % to 500 mol %©, and more preferably 350 mol % to 450 mol % with respect to the compound of formula (I).

[Total Amount of Water Contained in Materials Used in Reaction]

In the present invention, the total amount of water contained in the materials that are used in the reaction means the total amount of water contained in the alkali metal hydroxide, the alkanol, the compound of formula (I), the compound of formula (II), and other materials used in the reaction. When water is added during the reaction, the total amount of water contained in the materials that are used in the reaction means the sum of the amount of the water added and the amount of water contained in the alkali metal hydroxide, the alkanol, the compound of formula (I), the compound of formula (II), and compounds of other materials used in the reaction.

In the present invention, in the step of reacting the compound of formula (I) with the compound of formula (II) to provide the $\alpha,\beta$-unsaturated aldehyde of formula from the viewpoint of achieving high reaction efficiency while suppressing a side reaction, the total amount of water contained in the materials that are used in the reaction is 10 mol % or more, preferably 12.5 mol % or more, and more preferably 14 mol % or more with respect to the compound of formula (I). Furthermore, from the viewpoint of achieving high reaction efficiency while suppressing a side reaction, the amount of moisture is 50 mol % or less, preferably 30 mol % or less, and more preferably 25 mol % or less with respect to the compound of formula (I). The amount of moisture also includes moisture contained in the alkali metal hydroxide, the alkanol, the compound of formula (I), and the compound of formula (II). If the amount of moisture is outside the above specific range, the total amount of water contained in the compound of formula (II) and the compounds of other materials used in the reaction may be adjusted to 10 mol % or more and 50 mol % or less with respect to the compound of formula (I). The adjustment process may be performed by adding water to the materials used in the reaction. Alternatively, the adjustment process may be performed by using a material that previously contains water.

The amount of moisture in the system can be determined in the following manner. Each of the materials is measured by a Karl Fischer volumetric titration method, and then the amounts of moisture thus obtained are added together. Alternatively, the amount of moisture in the system can be determined by measuring a mixture of the materials.

In the present invention, the effect of containing a predetermined amount of moisture in the materials used in the reaction can be considered as follows. Due to the presence of a predetermined amount of moisture in the materials used in the reaction, the reaction solution changes from a homogeneous phase system to an oil-water two-phase system in the middle of the reaction, so that the reaction rate is relaxed.

When the amount of moisture is 10 mol % or more with respect to the compound of formula (I), the reaction activity is appropriate, and thus the disproportionation of the compound of formula (II) can be suppressed. Accordingly, this range is deemed to be preferable. On the other hand, when the amount of moisture is 50 mol % or less with respect to the compound of formula (I), the reaction to provide the $\alpha,\beta$-unsaturated aldehyde of formula (III) proceeds sufficiently before the reaction rate is relaxed, and thus the dimerization of the compound of formula (I) can be suppressed. Accordingly, this range is deemed to be preferable. In other words, the amount of moisture that falls in the range of 10 mol % to 50 mol % with respect to the compound of formula (I) may be advantageous for the following reasons. Since the reaction to provide the $\alpha,\beta$-unsaturated aldehyde of formula (III) proceeds rapidly, the dimerization of the compound of formula (I) is suppressed. Then, the reaction solution changes to the oil-water two-phase system, which relaxes the reaction rate. Therefore, while the disproportionation of the compound of formula (II) is suppressed, the reaction to provide the $\alpha,\beta$-unsaturated aldehyde of formula (III) is completed. Consequently, the $\alpha,\beta$-unsaturated aldehyde of formula (III) can be prepared with a high yield.

[Reaction Step]

In the present invention, from the viewpoint of reaction efficiency, the step of reacting the compound of formula (I) with the compound of formula (II) to provide the $\alpha,\beta$-unsaturated aldehyde of formula (III) is performed preferably at 20° C. or more, and more preferably at 25° C. or more. Furthermore, this step is performed preferably at 50° C. or less, and more preferably at 40° C. or less.

In the present invention, from the viewpoint of reaction efficiency, the step of reacting the compound of formula (I) with the compound of formula (II) to provide the $\alpha,\beta$-unsaturated aldehyde of formula (III) may be performed in an atmosphere of inert gas. From the viewpoint of reaction efficiency, the inert gas is preferably nitrogen or noble gas (elements in Group 18), and more preferably nitrogen. The noble gas may be, e.g., argon or helium and is preferably argon.

In the present invention, the step of reacting the compound of formula (I) with the compound of formula (II) to provide the $\alpha,\beta$-unsaturated aldehyde of formula (III) may be performed in the following manner. First, a solution in which the alkali metal hydroxide is dissolved in the alkanol is placed in a reaction vessel. Then, the compound of formula (II) is placed in the reaction vessel. Subsequently, the compound of formula (I) is added dropwise to the mixture thus obtained. In such a case, e.g., the compound of formula (I) may be added dropwise to a mixture of the alkanol, the alkali metal hydroxide, and the compound of formula (II). This is because the concentration of the compound of formula (I) in the reaction system is kept low by the dropwise addition of the compound of formula (I) to the reaction system, so that the dimerization of the compound of formula (I) can be suppressed. At the start of chopping, the total amount of water contained in the materials that are used in the reaction is adjusted to 10 mol % or more and 50 mol % or less with respect to the compound of formula (I). Specifically, the compound of formula (I) may be dropped for 3 hours or more and 9 hours or less, and preferably for 5 hours or more and 7 hours or less from the viewpoint of reaction efficiency.

When the compound of formula (I) is added dropwise to the mixture of the alkanol, the alkali metal hydroxide, and the compound of formula (II), the drop rate may be changed in multiple stages. The multiple stages may be two stages.

From the viewpoint of reaction efficiency, a relatively large amount of the compound of formula (I) may be added for a predetermined period of time, and then a relatively small amount of the compound of formula (I) may be added for a predetermined period of time. Specifically, the compound of formula (I) may be added dropwise by changing the chop rate in multiple stages. More specifically, 55% by mass or more and 85% by mass or less of the whole amount of addition of the compound of formula (I) may be added during one half (i.e., the first half period) of the drop time, and 15% by mass or more and 45% by mass or less of the whole amount of addition of the compound of formula (I) may be added during the other half (i.e., the second half period) of the drop time. Moreover, the drop rate during one half (i.e., the first half period) of the drop time may remain constant, while the drop rate during the other half (i.e., the second half period) of the drop time may be different from that in the first half period and may remain constant. When the drop rate is changed in two stages in the drop time, the drop rate during the other half (i.e., the second half period) of the drop time is preferably 0.2 times or more, more preferably 0.3 times or more, and further preferably 0.4 times or more the chop rate during one half (i.e., the first half period) of the drop time. Furthermore, the drop rate during the other half (i.e., the second half period) of the drop time is preferably 0.9 times or less, more preferably 0.8 times or less, and further preferably 0.7 times or less the drop rate during one half (i.e., the first half period) of the drop time.

In the present invention, when the step of reacting the compound of formula (I) with the compound of formula (II) to provide the α,β-unsaturated aldehyde of formula (III) is performed by placing a solution in which the alkali metal hydroxide is dissolved in the alkanol in a reaction vessel, then placing the compound of formula (II) in the reaction vessel, and adding the compound of formula (I) dropwise to the mixture thus obtained, the discharge portion of the compound of formula (I) may be located above the reaction solution or inside the reaction solution.

In the present invention, when the step of reacting the compound of formula (I) with the compound of formula (II) to provide the α,β-unsaturated aldehyde of formula (III) is performed by placing a solution in which the alkali metal hydroxide is dissolved in the alkanol in a reaction vessel, then placing the compound of formula (II) in the reaction vessel, and adding the compound of formula (I) dropwise to the mixture thus obtained, stirring may be continued for a certain time after the completion of the addition of the compound of formula (I) in order to terminate the reaction between the compound of formula (I) and the compound of formula (II). Specifically, the stirring may be performed preferably for 10 minutes or more, and more preferably for 20 minutes or more. Furthermore, the stirring may be performed preferably for 60 minutes or less, and more preferably for 45 minutes or less.

In the present invention, after performing the step of reacting the compound of formula (I) with the compound of formula (II) to provide the α,β-unsaturated aldehyde of formula (III), an acid compound may be added to the reaction vessel so that the alkali metal hydroxide is neutralized to stop the reaction, thereby avoiding the production of by-products. The acid compound may be, e.g., sulfuric acid, nitric acid, phosphoric acid, formic acid, acetic acid, propionic acid, or a solution thereof.

Concerning the above embodiments, the present invention further discloses a method for preparing an α,β-unsaturated aldehyde as follows.

<1> A method for preparing an α,β-unsaturated aldehyde, comprising a step of reacting a compound of formula (I) with a compound of formula (II) to provide an α,β-unsaturated aldehyde of formula (III), wherein an alkali metal hydroxide and an alkanol having 1 to 4 carbon atoms are used in the step, an amount of the alkali metal hydroxide is 8 mol % or more and 12 mol % or less with respect to the compound of formula (I), and a total amount of water contained in materials that are used in the reaction (i.e., the total amount of water contained in the alkali metal hydroxide, the alkanol, the compound of formula (I), the compound of formula (II), and other materials used in the reaction; when water is added during the reaction, it means the sum of the amount of the water added and the amount of water contained in the alkali metal hydroxide, the alkanol, the compound of formula (I), the compound of formula (II), and compounds of other materials used in the reaction) is 10 mol % or more and 50 mol % or less with respect to the compound of formula (I).

[Chemical Formula 4]

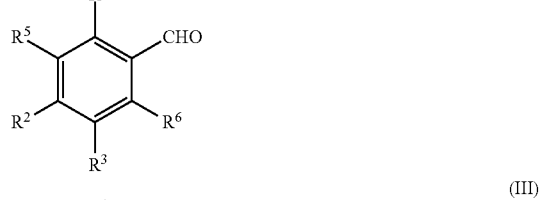

In the above formula, $R^1$ represents a hydrogen atom or an alkyl group having 1 to 10 carbon atoms, $R^2$ represents a hydrogen atom, an alkyl group having 1 to 6 carbon atoms, or an alkoxy group having 1 to 6 carbon atoms, $R^3$ represents a hydrogen atom, or $R^2$ and $R^3$ form 1,3-dioxolane together with carbon atoms to which $R^2$ and $R^3$ are bound, and $R^4$, $R^5$, and $R^6$ each independently represent a hydrogen atom or an alkyl group having 1 to 3 carbon atoms.

<2> A method for preparing an α,β-unsaturated aldehyde, comprising a step of reacting a compound of formula (I) with a compound of formula (II) to provide an α,β-unsaturated aldehyde of formula (III), wherein an alkali metal hydroxide and an alkanol having 1 to 4 carbon atoms are used in the step, an amount of the alkali metal hydroxide is 8 mol % or more and 12 mol % or less with respect to the compound of formula (I), and the step is performed so that a total amount of water contained in materials that are used in the reaction (i.e., the total amount of water contained in the alkali metal hydroxide, the alkanol, the compound of formula (I), the compound of formula (II), and other materials used in the reaction; when water is added during the reaction, it means the sum of the amount of the water added and the amount of water contained in the alkali metal hydroxide, the alkanol, the compound of formula (I), the compound of formula (II), and compounds of other materials used in the reaction) is adjusted to 10 mol % or more and 50 mol % or less with respect to the compound of formula (I).

[Chemical Formula 5]

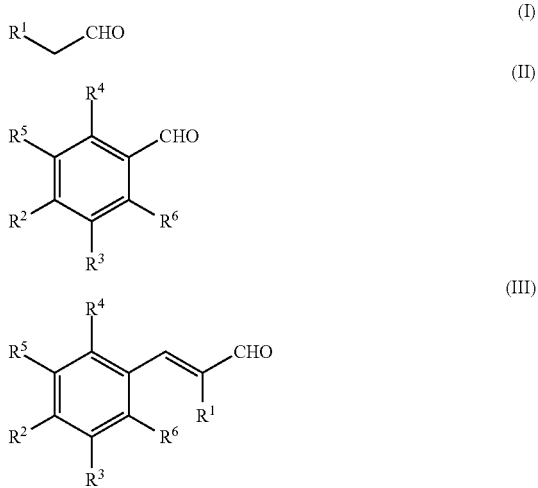

In the above formula, $R^1$ represents a hydrogen atom or an alkyl group having 1 to 10 carbon atoms, $R^2$ represents a hydrogen atom, an alkyl group having 1 to 6 carbon atoms, or an alkoxy group having 1 to 6 carbon atoms, $R^3$ represents a hydrogen atom, or $R^2$ and $R^3$ form 1,3-dioxolane together with carbon atoms to which $R^2$ and $R^3$ are bound, and $R^4$, $R^5$, and $R^6$ each independently represent a hydrogen atom or an alkyl group having 1 to 3 carbon atoms.

<3> The method for preparing the α,β-unsaturated aldehyde according to <1> or <2>, wherein an amount of the compound of formula (II) used in the step is preferably 1 equivalent or more, and more preferably 1.5 equivalents or more with respect to the compound of formula (I) and is also preferably 5 equivalents or less, and more preferably 3 equivalents or less with respect to the compound of formula (I).

<4> The method for preparing the α,β-unsaturated aldehyde according to any one of <1> to <3>, wherein the total amount of water contained in the materials that are used in the reaction is preferably 12.5 mol % or more, and more preferably 14 mol % or more with respect to the compound of formula (I) and is also preferably 30 mol % or less, and more preferably 25 mol % or less with respect to the compound of formula (I).

<5> The method for preparing the α,β-unsaturated aldehyde according to any one of <1> to <4>, wherein the total amount of water contained in the materials that are used in the reaction is 12.5 mol % or more and 30 mol % or less with respect to the compound of formula (I).

<6> The method for preparing the α,β-unsaturated aldehyde according to any one of <1> to <5>, wherein the total amount of water contained in the materials that are used in the reaction is 14 mol % or more and 25 mol % or less with respect to the compound of formula (I).

<7> The method for preparing the α,β-unsaturated aldehyde according to any one of <1> to <6>, wherein $R^1$ is preferably an alkyl group having 1 to 10 carbon atoms, and the alkyl group having 1 to 10 carbon atoms is preferably an alkyl group having 2 to 8 carbon atoms, more preferably an alkyl group having 3 to 8 carbon atoms, and further preferably an alkyl group having 3 to 7 carbon atoms.

<8> The method for preparing the α,β-unsaturated aldehyde according to any one of <1> to <7>, wherein the compound of formula (I) is acetaldehyde, propionaldehyde, butanal, pentanal, hexanal, heptanal, octanal, nonanal, decanal, or dodecanal, preferably propionaldehyde, butanal, pentanal, hexanal, heptanal, octanal, nonanal, or decanal, more preferably pentanal, hexanal, heptanal, octanal, nonanal, or decanal, and even more preferably pentanal, hexanal, heptanal, octanal, or nonanal.

<9> The method for preparing the α,β-unsaturated aldehyde according to any one of <1> to <8>, wherein $R^2$ is preferably a hydrogen atom or an alkyl group having 1 to 6 carbon atoms, and more preferably a hydrogen atom group.

<10> The method for preparing the α,β-unsaturated aldehyde according to any one of <1> to <9>, wherein the alkyl group represented by $R^2$ is preferably an alkyl group having 1 to 5 carbon atoms, and more preferably an alkyl group having 1 to 4 carbon atoms.

<11> The method for preparing the α,β-unsaturated aldehyde according to any one of <1> to <10>, wherein the alkoxy group represented by $R^2$ is preferably an alkoxy group having 1 to 5 carbon atoms, and more preferably an alkoxy group having 1 to 4 carbon atoms.

<12> The method for preparing the α,β-unsaturated aldehyde according to any one of <1> to <11>, wherein $R^3$, $R^4$, and $R^5$ are preferably hydrogen atoms.

<13> The method for preparing the α,β-unsaturated aldehyde according to any one of <1> to <12>, wherein the compound of formula (II) is a compound represented by any one of the following formulas.

[Chemical Formula 6]

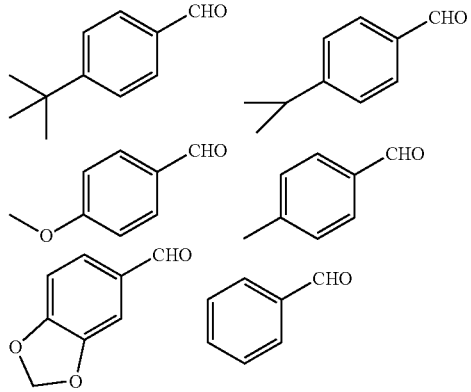

<14> The method for preparing the α,β-unsaturated aldehyde according to any one of <1> to <12>, wherein $R^1$ represents an alkyl group having 2 to 8 carbon atoms, $R^2$ represents hydrogen or an alkyl group having 1 to 5 carbon atoms, and $R^3$ to $R^6$ represent hydrogen.

<15> The method for preparing the α,β-unsaturated aldehyde according to any one of <1> to <12> and <14>, wherein $R^1$ represents an alkyl group having 2 to 8 carbon atoms, $R^2$ represents hydrogen or an alkyl group having 1 to 3 carbon atoms, and $R^3$ to $R^6$ represent hydrogen.

<16> The method for preparing the α,β-unsaturated aldehyde according to any one of <1> to <12>, wherein $R^1$ represents an alkyl group having 2 to 8 carbon atoms, and $R^2$ to $R^6$ represent hydrogen.

<17> The method for preparing the α,β-unsaturated aldehyde according to any one of <1> to <16>, wherein the step includes adding the compound of formula (I) dropwise to a mixture of the alkanol, the alkali metal hydroxide, and the compound of formula (II).

<18> The method for preparing the α,β-unsaturated aldehyde according to any one of <1> to <17>, wherein the alkali metal hydroxide is preferably lithium hydroxide, sodium hydroxide, or potassium hydroxide, more preferably sodium hydroxide or potassium hydroxide, and further preferably potassium hydroxide.

<19> The method for preparing the α,β-unsaturated aldehyde according to any one of <1> to <18>, wherein an amount of the alkali metal hydroxide is preferably 9 mol % or more and preferably 11 mol % or less with respect to the compound of formula (I).

<20> The method for preparing the α,β-unsaturated aldehyde according to any one of <1> to <19>, wherein the amount of the alkali metal hydroxide is 8.5 mol % or more and 11.5 mol % or less with respect to the compound of formula W, and the total amount of water is 14 mol % or more and 30 mol % or less with respect to the compound of formula (I).

<21> The method for preparing the α,β-unsaturated aldehyde according to any one of <1> to <19>, wherein the amount of the alkali metal hydroxide is 8.5 mol % or more and 11.5 mol % or less with respect to the compound of formula W, and
the total amount of water is 12.5 mol % or more and 30 mol % or less with respect to the compound of formula (I).

<22> The method for preparing the α,β-unsaturated aldehyde according to any one of <1> to <19>, wherein the amount of the alkali metal hydroxide is 8.5 mol % or more and 11.5 mol % or less with respect to the compound of formula a and
the total amount of water is 14 mol % or more and 25 mol % or less with respect to the compound of formula (I).

<23> The method for preparing the α,β-unsaturated aldehyde according to any one of <1> to <22>, wherein the alkanol is preferably an alkanol having 1 to 3 carbon atoms, and more preferably an alkanol having 1 to 2 carbon atoms.

<24> The method for preparing the α,β-unsaturated aldehyde according to any one of <1> to <23>, wherein an amount of the alkanol having 1 to 4 carbon atoms is preferably 300 mol % to 500 mol %, and more preferably 350 mol % to 450 mol % with respect to the compound of formula (I).

<25> The method for preparing the α,β-unsaturated aldehyde according to any one of <1> to <24>, wherein the step of reacting the compound of formula (I) with the compound of formula (II) to provide the α,β-unsaturated aldehyde of formula (III) is performed preferably at 20° C. or more, and more preferably at 25° C. or more and also performed preferably at 50° C. or less, and more preferably at 40° C. or less.

<26> The method for preparing the α,β-unsaturated aldehyde according to any one of <1> to <25>, wherein the step of reacting the compound of formula (I) with the compound of formula (II) to provide the α,β-unsaturated aldehyde of formula (III) is performed in an atmosphere of inert gas (preferably nitrogen or noble gas (elements in Group 18, including, e.g., argon and helium, and preferably argon), and more preferably nitrogen), <27> The method for preparing the α,β-unsaturated aldehyde according to any one of <17> to <26>, wherein the compound of formula (I) is added dropwise for a drop time of preferably 3 hours or more and 9 hours or less, and more preferably 5 hours or more and 7 hours or less.

<28> The method for preparing the α,β-unsaturated aldehyde according to any one of <17> to <27>, wherein the compound of formula (I) is added dropwise by changing a drop rate in multiple stages.

<29> The method for preparing the α,β-unsaturated aldehyde according to any one of <17> to <28>, wherein the compound of formula (I) is added dropwise by changing the drop rate in two stages.

<30> The method for preparing the α,β-unsaturated aldehyde according to <29>, wherein the two stages include a stage corresponding to a first half period of the drop time and a stage corresponding to a second half period of the drop time, and
the drop rate during the second half period (the second half period) of the drop time is preferably 0.2 times or more, more preferably 0.3 times or more, and further preferably 0.4 times or more the drop rate during the first half period (the first half period) of the drop time and is also preferably 0.9 times or less, more preferably 0.8 times or less, and further preferably 0.7 times or less the drop rate during one half (the first half period) of the drop time.

<31> The method for preparing the α,β-unsaturated aldehyde according to <29> or <30>, wherein the two stages include a stage corresponding to a first half period of the drop time and a stage corresponding to a second half period of the drop time, and
the compound of formula (I) is added dropwise so that 55% by mass or more and 85% by mass or less of the whole amount of addition of the compound of formula (I) is added during one half (the first half period) of the chop time, and 15% by mass or more and 45% by mass or less of the whole amount of addition of the compound of formula (I) is added during the other half of the drop time.

<32> The method for preparing the α,β-unsaturated aldehyde according to any one of <1> to <31>, wherein when the step of reacting the compound of formula (I) with the compound of formula (II) to provide the α,β-unsaturated aldehyde of formula (III) is performed by placing a solution in which the alkali metal hydroxide is dissolved in the alkanol in a reaction vessel, then placing the compound of formula (II) in the reaction vessel, and adding the compound of formula (I) dropwise to the mixture thus obtained, a discharge portion of the compound of formula (I) is located above the reaction solution or inside the reaction solution.

<33> The method for preparing the α,β-unsaturated aldehyde according to any one of <1> to <32>, wherein when the step of reacting the compound of formula (I) with the compound of formula (II) to provide the α,β-unsaturated aldehyde of formula (III) is performed by placing a solution in which the alkali metal hydroxide is dissolved in the alkanol in a reaction vessel, then placing the compound of formula (II) in the reaction vessel, and adding the compound of formula (I) dropwise to the mixture thus obtained, stirring is performed for a certain time, preferably for 10 minutes to 60 minutes, and more preferably for 20 minutes to 45 minutes after completion of the addition of the compound of formula (I).

<34> The method for preparing the α,β-unsaturated aldehyde according to any one of <1> to <33>, wherein after performing the step of reacting the compound of formula (I) with the compound of formula (II) to provide the α,β-unsaturated aldehyde of formula (III), an acid compound (preferably sulfuric acid, nitric acid, phosphoric acid, formic acid, acetic acid, propionic acid, or a solution thereon is added to the reaction vessel so that the alkali metal hydroxide is neutralized to stop the reaction, thereby avoiding the production of by-products.

EXAMPLES

In the following examples and comparative examples, unless otherwise specified, the term "%" means "% by mass."

The materials used in the reaction were as follows:

benzaldehyde: manufactured by Wako Pure Chemical industries, Ltd., Wake special grade;

octanal: manufactured by Kao Corporation;

methanol: manufactured by Wake Pure Chemical Industries, Ltd., Wako special grade;

potassium hydroxide: manufactured by Wake Pure Chemical Industries, Ltd., Wako special grade;

acetic acid: manufactured by Wako Pure Chemical Industries, Ltd., Wako special grade;

tetradecane: manufactured by Wako Pure Chemical Industries, Ltd., Wako special grade; and diethyl ether: manufactured by Wako Pure Chemical Industries, Ltd., Wako special grade.

The concentration of moisture in each of the materials was determined by a volumetric titration method using a Karl Fischer moisture titrator MKV-710 (manufactured by Kyoto Electronics Manufacturing Co., Ltd.). The titration solvent was KEMAQUA Dehydrating Solvent KET (manufactured by Kyoto Electronics Manufacturing Co., Ltd.). The titrant was KEMAQUA Titrant TR-3 (manufactured by Kyoto Electronics Manufacturing Co., Ltd.).

Example 1

Preparation of hexyl cinnamic aldehyde (formula (III-1))

[Chemical Formula 7]

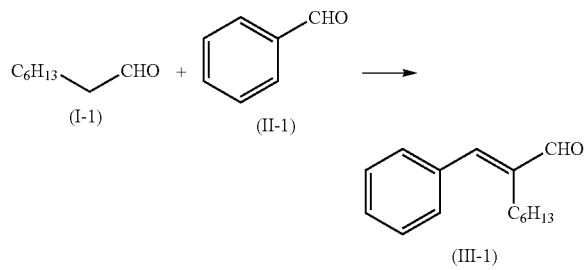

First, methanol (128.2 g, 4.0 mol, 400 mol % with respect to octanal, moisture content: 0.04%, amount of moisture: 0.05 g) and water (2.6 g) were mixed. Then, potassium hydroxide (purity: 85%, 6.6 g, 0.10 mol, 10 mol % with respect to octanal, moisture content: 15%, amount of moisture: 0.99 g) was dissolved in the liquid mixture, and a potassium hydroxide-methanol solution (137.1 g) was prepared. A thermometer, a mechanical stirrer, a condenser, and a nitrogen line were attached to a 500 mL four-necked separable flask and thus assembled into a reactor.

The potassium hydroxide-methanol solution (137.1 g) and benzaldehyde (formula (II-1), 180.4 g, 1.70 mol, 170 mol % with respect to octanal, moisture content; 0.05%, amount of moisture: 0.09 g) were added to the reactor. Subsequently, a 200 mL flask containing octanal (formula (I-1)) was connected to the reactor via a dropping pump. The inside of the reactor was replaced with nitrogen. The reactor was placed in a warm bath at 30° C., and stirring (500 rpm) of the contents in the reactor was started. After 5 minutes passed, dropping of octanal into the reactor was started. The octanal was drooped into the reactor at 25.6 g/hour for 3 hours, and then at 17.1 g/hour for 3 hours. Thus, it took a total of 6 hours to drop the octanal (128.2 g, 1.0 mol, amount of moisture: 0 g) into the reactor. The total amount of water contained in the materials that were used in the reaction was 3.73 g (20.7 mol % with respect to octanal). The stirring of the contents in the reactor was continued at 30° C. for 0.5 hours after the dropping of the octanal was completed. Then, acetic acid (5.0 g, 0.08 mol, 8.3 mol % with respect to octanal) was added to the reactor to stop the reaction in the reactor, so that the reaction was finished.

Using gas chromatography (GC), a quantitative analysis of the reaction product was performed by an internal standard method to determine the composition for each component of the reaction product. The results of the reaction were calculated by the following formulas based on the composition of the reaction product thus obtained. The internal standard substance was tetradecane, and the solvent was diethyl ether. Table 1 shows the calculated dimer formation rate and selectivity of hexyl cinnamic aldehyde (with respect to benzaldehyde).

Specifically, 0.3 mL of the reaction solution was sampled, put in a screw bottle, and precisely weighed. Then, 0.1 g of tetradecane was added to the reaction solution and precisely weighed. Moreover, 1 mL of a phosphate buffer and 3 mL of ether were added to the reaction solution and shaken. This liquid was allowed to stand still so that oil was separated from water. The upper layer was analyzed by GC.

The GC analysis used both DB-1 column (GC column, 100% dimethylpolysiloxane, manufactured by Agilent Technologies Japan, Ltd.) and DB-WAX column (GC column, polyethylene glycol, manufactured by Agilent Technologies Japan, Ltd.).

[Dimer Formation Rate]

A dimer formation rate, which is a measure of the dimerization of aldehydes, was calculated by the following formula. A smaller value indicates better performance.

Dimer formation rate [%]=[GC area of dimer in product]/[GC area % of hexyl cinnamic aldehyde in product]

[Selectivity of Hexyl Cinnamic Aldehyde (with Respect to Benzaldehyde)]

A selectivity of hexyl cinnamic aldehyde (with respect to benzaldehyde), which is a measure of the disproportionation of aldehydes, was calculated by the following formula. A larger value indicates better performance.

Selectivity of hexyl cinnamic aldehyde (with respect to benzaldehyde) [%]=([mass of hexyl cinnamic aldehyde in product]/[molecular weight of hexyl cinnamic aldehyde])/{([mass of benzaldehyde introduced]−[mass of benzaldehyde in product])/[molecular weight of benzaldehyde]}×100

Example 2

Example 2 was performed in the same manner as Example 1 except that the amount of potassium hydroxide was changed from 10 mol % to 12 mol % with respect to octanal, and the total amount of water contained in the materials that were used in the reaction was changed from 20.7 mol % to 21.4 mol % with respect to octanal. Table 1 shows the results of the evaluation of the product thus obtained.

Example 3

Example 3 was performed in the same manner as Example 1 except that the amount of potassium hydroxide was changed from 10 mol % to 8 mol % with respect to octanal, and the total amount of water contained in the materials that were used in the reaction was changed from 20.7 mol % to 19.2 mol % with respect to octanal. Table 1 shows the results of the evaluation of the product thus obtained.

Comparative Examples 1 to 3

Comparative Examples 1 to 3 were performed in the same manner as Example 1 except that the amount of potassium hydroxide and the total amount of water contained in the materials that were used in the reaction were changed as shown in Table 1. Table 1 shows the results of the evaluation of the products thus obtained. In Table 1, the amount of potassium hydroxide (KOH equivalent) represents a mole percent (mol %) with respect to octanal. In Table 1, the total amount of water contained in the materials that were used in the reaction, which was the sum of the amount of moisture contained in methanol, potassium hydroxide, and benzaldehyde and the amount of moisture added separately to the reactor, represents a mole percent (mol %) with respect to octanal.

Table 1 shows the reaction conditions and the results in Examples 1 to 3 and Comparative Examples 1 to 3.

TABLE 1

|  | KOH equivalent (mol %) | Total amount of water contained in materials used in reaction (mol %) | Selectivity of hexyl cinnamic aldehyde (with respect to benzaldehyde) (%) | Dimer formation rate (%) |
|---|---|---|---|---|
| Comp. Ex. 1 | 6 | 18.6 | 93.7 | 1.30 |
| Ex. 3 | 8 | 19.2 | 92.5 | 1.01 |
| Ex. 1 | 10 | 20.7 | 93.8 | 0.89 |
| Ex. 2 | 12 | 21.4 | 92.3 | 1.00 |
| Comp. Ex. 2 | 14 | 22.8 | 88.0 | 0.74 |
| Comp. Ex. 3 | 17 | 24.9 | 87.9 | 0.67 |

Example 4

Example 4 was performed in the same manner as Example 1 except that the total amount of water contained in the materials that were used in the reaction was changed from 20.7 mol % to 13.5 mol % with respect to octanal. Table 2 shows the results of the evaluation of the product thus obtained.

Example 5

Example 5 was performed in the same manner as Example 1 except that the 1.5 total amount of water contained in the materials that were used in the reaction was changed from 20.7 mol % to 27.7 mol % with respect to octanal. Table 2 shows the results of the evaluation of the product thus obtained.

Example 6

Example 6 was performed in the same manner as Example 1 except that the total amount of water contained in the materials that were used in the reaction was changed from 20.7 mol % to 42.0 mol % with respect to octanal. Table 2 shows the results of the evaluation of the product thus obtained.

Comparative Examples 4 to 9

Comparative Examples 4 to 9 were performed in the same manner as Example 1 except that the amount of potassium hydroxide and the total amount of water contained in the materials that were used in the reaction were changed as shown in Table 2. Table 2 shows the results of the evaluation of the products thus obtained. In Table 2, the amount of potassium hydroxide (KOH equivalent) represents a mole percent (mol %) with respect to octanal. In Table 2, the total amount of water contained in the materials that were used in the reaction, which was the sum of the amount of moisture contained in methanol and potassium hydroxide and the amount of moisture added separately to the reactor, represents a mole percent (mol %) with respect to octanal.

TABLE 2

|  | KOH equivalent (mol %) | Total amount of water contained in materials used in reaction (mol %) | Selectivity of hexyl cinnamic aldehyde (with respect to benzaldehyde) (%) | Dimer formation rate (%) |
|---|---|---|---|---|
| Comp. Ex. 4 | 10 | 6.4 | 88.4 | 0.83 |
| Comp. Ex. 5 | 10 | 8.5 | 88.1 | 0.86 |
| Comp. Ex. 6 | 10 | 9.3 | 87.9 | 0.85 |
| Ex. 4 | 10 | 13.5 | 92.4 | 0.79 |
| Ex. 5 | 10 | 27.7 | 93.4 | 0.91 |
| Ex. 6 | 10 | 42.0 | 93.1 | 1.01 |
| Comp. Ex. 7 | 10 | 77.6 | 89.4 | 1.15 |

TABLE 2-continued

| | KOH equivalent (mol %) | Total amount of water contained in materials used in reaction (mol %) | Selectivity of hexyl cinnamic aldehyde (with respect to benzaldehyde) (%) | Dimer formation rate (%) |
|---|---|---|---|---|
| Comp. Ex. 8 | 10 | 131.1 | 92.3 | 1.56 |
| Comp. Ex. 9 | 10 | 184.6 | 94.0 | 2.11 |

The results in Tables 1 and 2 confirmed that when the compound of formula (I) was reacted with the compound of formula (II) to provide the α,β-unsaturated aldehyde of formula the selectivity of the α,β-unsaturated aldehyde (with respect to the compound of formula (II)) was high and the dimer formation rate was low under the condition that the total amount of water contained in the materials that were used in the reaction was 10 mol % to 50 mol % with respect to the compound of formula (I), the amount of the alkali metal hydroxide was 8 mol % to 12 mol % with respect to the compound of formula (I), and alkanol having 1 to 4 carbon atoms was used.

INDUSTRIAL APPLICABILITY

The preparation method of the present invention can prepare a target aldehyde with high selectivity and also can suppress the production of by-products. Therefore, the α,β-unsaturated aldehyde can be prepared with high efficiency and high purity. The preparation method of the present invention can be suitably used as a method for preparing an aldehyde that is useful as a fragrance material.

The invention claimed is:

1. A method for preparing an α,β-unsaturated aldehyde, comprising:
reacting a compound of formula (I) with a compound of formula (II) to provide an α,β-unsaturated aldehyde of formula (III)
in the presence of an alkali metal hydroxide and an alkanol having 1 to 4 carbon atoms,
wherein an amount of the alkali metal hydroxide is 8 mol % or more and 12 mol % or less with respect to an amount of the compound of formula (I), and
a total amount of water contained in materials that are used in the reaction is 10 mol % or more and 50 mol % or less with respect to the amount of the compound of formula (I),

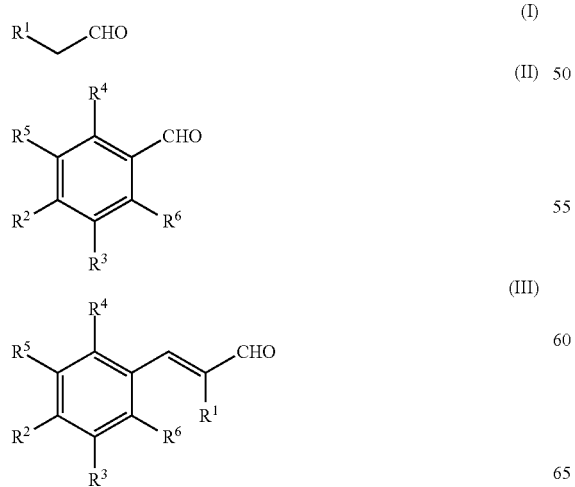

where $R^1$ represents a hydrogen atom or an alkyl group having 1 to 10 carbon atoms,
$R^2$ represents a hydrogen atom, an alkyl group having 1 to 6 carbon atoms, or an alkoxy group having 1 to 6 carbon atoms,
$R^3$ represents a hydrogen atom, or
$R^2$ and $R^3$ form 1,3-dioxolane together with carbon atoms to which $R^2$ and $R^3$ are bound, and
$R^4$, $R^5$, and $R^6$ each independently represent a hydrogen atom or an alkyl group having 1 to 3 carbon atoms.

2. The method for preparing the α,β-unsaturated aldehyde according to claim 1, wherein an amount of the compound of formula (II) used in the reaction is 1.5 equivalents or more with respect to the amount of the compound of formula (I).

3. The method for preparing the α,β-unsaturated aldehyde according to claim 1, wherein the total amount of water contained in the materials that are used in the reaction is 12.5 mol % or more and 30 mol % or less with respect to the amount of the compound of formula (I).

4. The method for preparing the α,β-unsaturated aldehyde according to claim 1, wherein $R^1$ represents an alkyl group having 3 to 8 carbon atoms.

5. The method for preparing the α,β-unsaturated aldehyde according to claim 1, wherein the compound of formula (II) is a compound represented by any one of the following formulas:

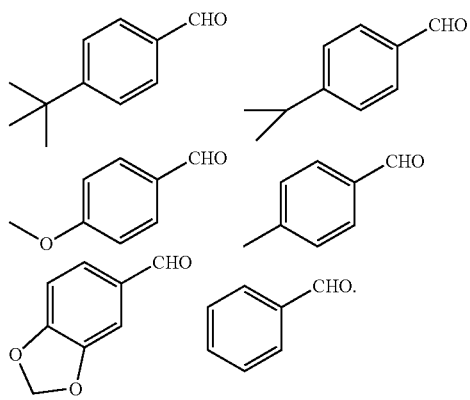

6. The method for preparing the α,β-unsaturated aldehyde according to claim 1, wherein the alkali metal hydroxide is lithium hydroxide, sodium hydroxide, or potassium hydroxide.

7. The method for preparing the α,β-unsaturated aldehyde according to claim 1, wherein the alkanol having 1 to 4 carbon atoms is methanol or ethanol.

8. The method for preparing the α,β-unsaturated aldehyde according to claim 1, wherein an amount of the alkanol having 1 to 4 carbon atoms is 300 mol % to 500 mol % with respect to the amount of the compound of formula (I).

9. The method for preparing the α,β-unsaturated aldehyde according to claim 1, wherein the reaction includes adding the compound of formula (I) dropwise to a mixture of the alkanol, the alkali metal hydroxide, and the compound of formula (II).

10. The method for preparing the α,β-unsaturated aldehyde according to claim 9, wherein the compound of formula (I) is added dropwise for a drop time of 3 hours or more and 9 hours or less.

11. The method for preparing the α,β-unsaturated aldehyde according to claim 9, wherein the compound of formula (I) is added dropwise by changing a drop rate in multiple stages.

12. The method for preparing the α,β-unsaturated aldehyde according to claim 9, wherein the compound of formula (I) is added dropwise by changing a drop rate in two stages.

13. The method for preparing the α,β-unsaturated aldehyde according to claim 12, wherein the two stages include a stage corresponding to a first half period of a drop time and a stage corresponding to a second half period of the drop time, and the drop rate during the second half period of the drop time is 0.2 times or more and 0.9 times or less the drop rate during the first half period of the drop time.

\* \* \* \* \*